US012741262B2

(12) United States Patent
Kung et al.

(10) Patent No.: US 12,741,262 B2
(45) Date of Patent: Sep. 22, 2026

(54) SYSTEM AND METHOD FOR THE CONTROL OF BIOMASS CONVERSION SYSTEMS

(71) Applicant: Takachar Limited, Richmond, CA (US)

(72) Inventors: Kevin S. Kung, Richmond, CA (US); Vidyut Mohan, New Delhi (IN)

(73) Assignee: Takachar Limited, Richmond, CA (US)

( * ) Notice: Subject to any disclaimer, the term of this patent is extended or adjusted under 35 U.S.C. 154(b) by 1017 days.

(21) Appl. No.: 17/775,840

(22) PCT Filed: Nov. 11, 2020

(86) PCT No.: PCT/US2020/060011
§ 371 (c)(1),
(2) Date: May 10, 2022

(87) PCT Pub. No.: WO2021/096956
PCT Pub. Date: May 20, 2021

(65) Prior Publication Data

US 2023/0032416 A1 Feb. 2, 2023

Related U.S. Application Data

(60) Provisional application No. 62/985,701, filed on Mar. 5, 2020, provisional application No. 62/933,684, filed on Nov. 11, 2019.

(51) Int. Cl.

| | |
|---|---|
| ***B01J 19/00*** | (2006.01) |
| ***C05D 9/00*** | (2006.01) |
| ***C12M 1/34*** | (2006.01) |

(52) U.S. Cl.
CPC ......... *B01J 19/004* (2013.01); *B01J 19/0033* (2013.01); *C05D 9/00* (2013.01);
(Continued)

(58) Field of Classification Search
CPC .. B01J 19/0006; B01J 19/0033; B01J 19/004; B01J 2219/0038; B01J 2219/00164;
(Continued)

(56) References Cited

U.S. PATENT DOCUMENTS

| | | | |
|---|---|---|---|
| 6,015,496 | A | 1/2000 | Khudenko |
| 6,767,375 | B1 | 7/2004 | Pearson |

(Continued)

FOREIGN PATENT DOCUMENTS

| | | | |
|---|---|---|---|
| CN | 101805690 | B | 10/2012 |
| CN | 205590629 | U | 9/2016 |

(Continued)

*Primary Examiner* — Lessanework Seifu
(74) *Attorney, Agent, or Firm* — Alpine Patents LLC; Brian Van Osdol

(57) ABSTRACT

A system and method for a reactor-based biomass processing comprising: detecting a biomass input, comprising: detecting the biomass type, detecting the biomass quality, comprising detecting the biomass composition including the biomass moisture content, and detecting the biomass quantity; determining an optimized end-product, wherein the end-product is at least partially based on: a selected production target, the biomass input, and on local conditions; and producing the end-product, comprising: monitoring reaction conditions, configuring the reactor for the output production, based at least partially on biomass input, wherein configuring the reactor includes adjusting an oxygen flow rate into the reactor, and implementing a biomass decomposition.

14 Claims, 11 Drawing Sheets

(52) U.S. Cl.
CPC .... *C12M 41/36* (2013.01); *B01J 2219/00038* (2013.01); *B01J 2219/00164* (2013.01); *B01J 2219/00193* (2013.01); *B01J 2219/00198* (2013.01); *B01J 2219/00227* (2013.01)

(58) Field of Classification Search
CPC .... B01J 2219/00193; B01J 2219/00198; B01J 2219/00231; B01J 2219/00227; C05D 9/00; C05F 17/70; C05F 5/002
See application file for complete search history.

(56) References Cited

U.S. PATENT DOCUMENTS

| | | | |
|---|---|---|---|
| 7,097,762 | B1 | 8/2006 | Ruocco et al. |
| 2003/0223909 | A1 | 12/2003 | Oberbeck et al. |
| 2011/0258837 | A1 | 10/2011 | Scannon et al. |
| 2011/0278150 | A1 | 11/2011 | Mulqueen et al. |
| 2012/0107921 | A1 | 5/2012 | Willson et al. |
| 2013/0247448 | A1 | 9/2013 | Ampulski et al. |
| 2014/0157777 | A1 | 6/2014 | Kramer et al. |
| 2014/0332724 | A1 | 11/2014 | Tsangaris et al. |
| 2016/0053181 | A1 | 2/2016 | Ericsson et al. |
| 2016/0185633 | A1 | 6/2016 | Pullammanappallil et al. |
| 2017/0312731 | A1 | 11/2017 | Vu |
| 2019/0010069 | A1 | 1/2019 | Skardon |
| 2020/0017788 | A1 | 1/2020 | Endo et al. |

FOREIGN PATENT DOCUMENTS

| | | | | |
|---|---|---|---|---|
| EP | 2199375 | A2 | 6/2010 | |
| WO | WO-2018213474 | A1 * | 11/2018 | C05F 7/00 |
| WO | WO-2020169171 | A1 * | 8/2020 | C22B 1/02 |

* cited by examiner

SYSTEM AND METHOD FOR THE CONTROL OF BIOMASS CONVERSION SYSTEMS

CROSS-REFERENCE TO RELATED APPLICATIONS

This Application is a 371 National Stage Patent Application of PCT Application No. PCT/US20/60011, filed on 11 Nov. 2020, which claims the benefit of U.S. Provisional Application No. 62/933,684, filed on 11 Nov. 2019, and U.S. Provisional Application No. 62/985,701, filed on 5 Mar. 2020, all of which are incorporated in their entireties by this reference.

TECHNICAL FIELD

This invention relates generally to the field of real-time optimized biomass processing, and more specifically to a new and useful system and method for the control of biomass conversion systems.

BACKGROUND

Biomass is plant or animal material used for energy production, or in various processes as raw material for a range of products. Historically, humans have harnessed biomass-derived energy since the time people began burning wood fuel. Since then many processes have been developed to harness biomass in numerous ways.

Biomass may be harnessed using thermal conversions, that use heat, as the dominant mechanism to upgrade biomass into a better and more practical fuel. Biomass may also be converted to better a fuel source using torrefaction, pyrolysis, and gasification are other common methods. Chemical conversion may be used to convert biomass into other useful compounds (e.g. carbon-based products). Alternatively, biochemical conversions (e.g. fermentation) are used to breakdown biomass into useful molecules. Biomass can also be converted to electricity using electrochemical conversion, i.e. electrocatalytic oxidation. Electrochemical conversion may even be used to create microbial fuel cells.

As of now, there are many factories that process biomass in an industrialized fashion. Thus, both processed and unprocessed biomass is transported everywhere. With the industrialization and huge throughput highly specialized biomass processing to produce energy, smaller implementations of biomass processing have been left behind and mostly forgotten. Currently most biomass reactors are large systems with little to no control over the type of biomass input. These biomass reactors are simple reactors with little to no control of the output. Additionally, these large biomass reactors are centrally located and fixed, making transport of biomass from isolated areas difficult.

Thus, there is a need in the biomass conversion field to create a new and useful system and method for transportable, biomass reactors that can receive different types of biomass and harness biomass energy in different manners. This invention provides such a new and useful system and method.

DESCRIPTION OF THE EMBODIMENTS

Figure 1:
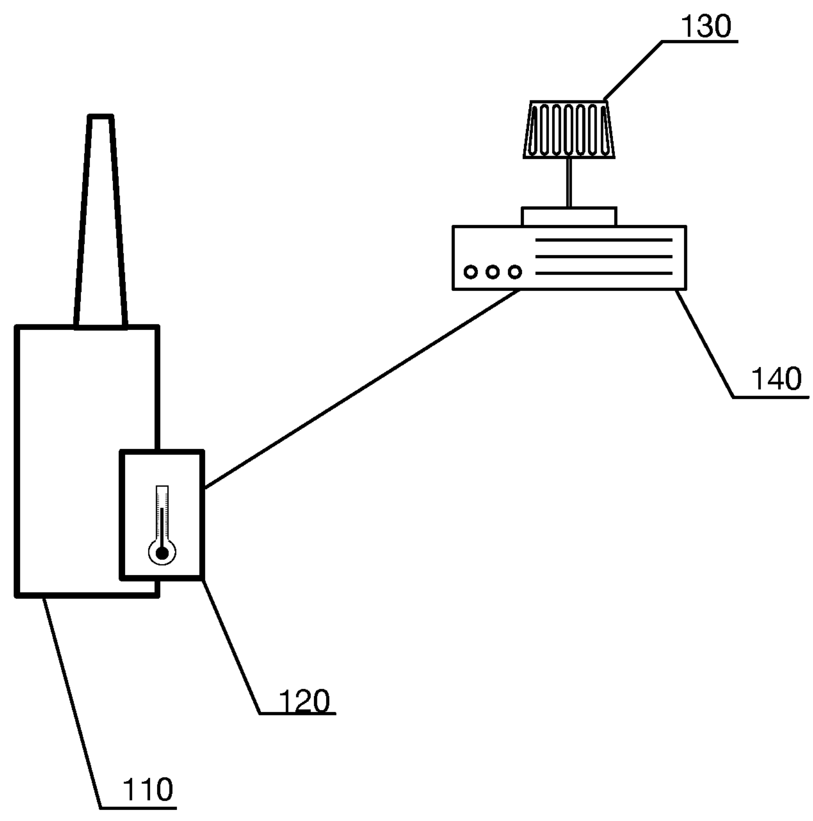
FIG. 1 is a schematic of a single reactor system.

The following description of the embodiments of the invention is not intended to limit the invention to these embodiments but rather to enable a person skilled in the art to make and use this invention.

1. Overview

A system and method for control of biomass processing includes: biomass reactors, that receives biomass and can output different end-products dependent on a control unit; and a control unit that determines the optimal end-product for the bioreactor dependent on market conditions. The system and method functions to provide control of dynamically adjustable biomass reactors. By leveraging obtained market information, biomass information, and bioreactor information, and/or other forms of data input, the control unit may determine an enhanced/optimized output dependent on a variety of conditions. The system and method may further include a network of bioreactors. The control unit may then determine optimal outputs for all reactors and thus output production for the entire network.

The system and method may have particular applicability for small portable bioreactors. In one implementation, the biomass reactor may be substantially similar to the biomass reactor device described in WO2018/213474A1, filed on 16 May 2018, which is hereby incorporated in its entirety by this reference. The system and method may additionally be applied to alternative or additional forms of transformation systems. In another exemplary application, the system and method are used with biomass reactors including small-scale, process-intensified pyrolysis reactors, wherein these biomass reactors produce liquid products (e.g. bio-oil, diesel, and other fractionated chemical compounds) as well as synthesis gas, from biomass. The system and method have general applicability to any and/or all types of biomass reactors of any size.

The system and method may provide particular use for "merchants" and private individuals. The system and method enable biomass processing for low operating costs, with the potential of an optimized output that may be either locally utilized and/or profitable.

The system and method provide the potential feature of a portable system that may be utilized in regions not easily accessible by large bioreactors. The various individuals using the biomass reactors may be enabled to independently operate the biomass reactors, while the complexity of determining how to operate the biomass reactors is handled by a remote control system that's able to coordinate with many factors like the makeup of the supplied biomass, market conditions, status of other biomass reactors on the network.

The system and method may provide a number of potential benefits. The system and method are not limited to always providing such benefits and are presented only as exemplary representations for how the system and method may be put to use. The list of benefits is not intended to be exhaustive and other benefits may additionally or alternatively exist.

The system and method provide the benefit of remote control of a bioreactor. Additionally, through an interface, the system and method enable diagnostic testing, analysis, troubleshooting, and providing maintenance inputs.

Remote testing may additionally enable quick verification of samples and thus a quick turnaround in processing flexibility.

The system and method may provide the benefit of a large array of implementations for different scopes of biomass processing. In this manner the system and method may enable highly customizable outputs for user needs.

The system and method may further incorporate regional data to increase and the level of customizability. For example, local weather and climate conditions may be incorporated to optimize end-products.

As time passes and local conditions change, the system and method may provide the benefit of dynamic variability to quickly optimize end-products. The system and method can enable a bioreactor to adjust to changing conditions. This may, in some variations, even be performed in substantially real-time (e.g., within minutes).

The system and method additionally provide a biomass reactor that can processes a multitude of biomasses. This may provide the benefit of enabling a single biomass reactor that can process material without the requirement of transporting biomass. It also serves to enable operators to supply the biomass that is readily available in the location where they are operating their biomass reactors.

Another potential benefit is that the system and method may process the biomass in a multitude of ways to produce a desired end-product. This may ensure that the biomass reactor does not becoming obsolete. Additionally, this benefit of the system and method may potentially prevent gluts or shortfalls due to inflexible production.

The system and method may potentially help with local environmental conditions. For example: the system and method may be used to reduce local forest residue to help reduce the possibility of fires.

The system and method may potentially improve waste management. As it may not always be feasible to transport waste from isolated areas, the system and method may enable processing and utilizing of local waste.

As another potential feature, the system and method may incorporate a network of biomass reactors. This network of biomass reactors can be controlled collectively. In one variation, a network of biomass reactors, operated by various parties. The system and method may facilitate coordinating the outputs of these biomass reactors. This coordination may be to increase profits or to optimize any suitable metric (e.g. reducing carbon emissions). For example, one subset of biomass reactors may be controlled to output a fertilizer base, while another subset of biomass reactors may be controlled so as to output biofuel. The control decision may be transparent to the operating entities.

This optimization may take into account geographical locations and the input biomass to optimize output even further. For example, biomass reactors near farms may be controlled to output fertilizer, wherein other biomass reactors may produce biofuel.

2. System

As shown in FIG. 1, a system for a dynamically optimized end-product production from a biomass include: a bioreactor 110, that stores and processes biomass; a sensor system 120, comprising internal sensors 122, sensor components on and within the bioreactor, and external sensors 124, sensor components employed away from the bioreactor; a communication unit 130, configured to send and receive communication from internal and external sources; and a control unit 140.

The system functions as a means to store and process diverse biomaterial in an optimized fashion. That is, the system can receive and store different types and quantities of biomass material, determine one or more optimal end-products for the biomass, and convert the biomass material into the optimal end-product. The optimal end-product may be determined from many factors, which may internal factors (e.g. type of biomass, biomass quantity, biomass moisture content, biomass pH, type of bioreactor 110) and/or external factors (e.g. market prices, weather conditions, soil conditions (e.g. pH), and user desired end-products).

Figure 2:
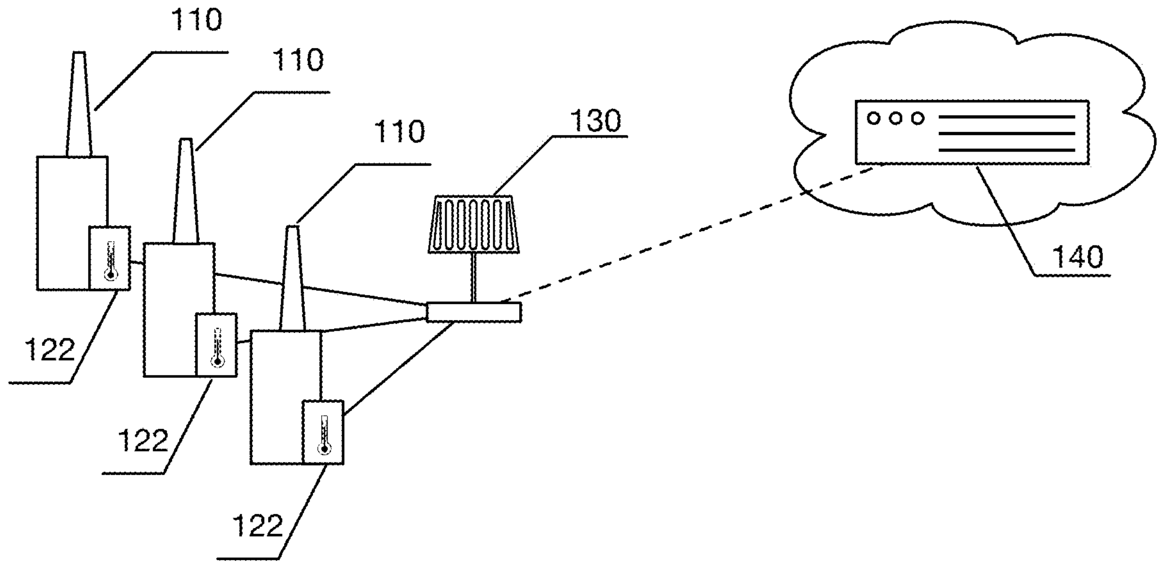
FIG. 2 is a variation schematic of a bioreactor network system.
Figure 3:
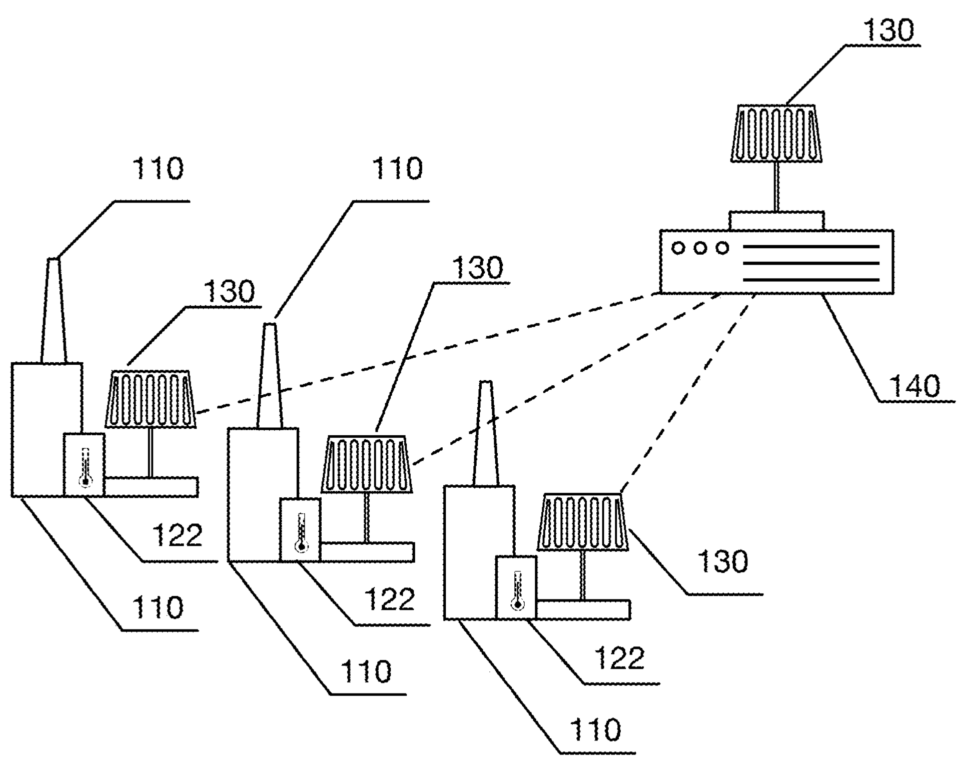
FIG. 3 is a variation schematic of a bioreactor network system.
Figure 4:
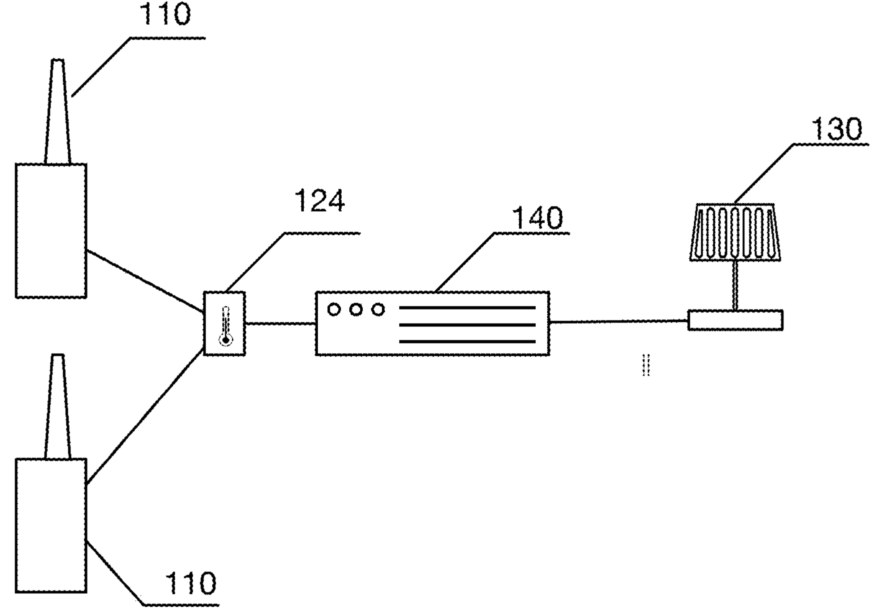
FIG. 4 is a variation schematic of a bioreactor network system.

As shown in FIGS. 2-4, the system may further comprise network variations, wherein the system comprises a plurality of bioreactors no (i.e. a network of bioreactors). The network of bioreactors no may include one or more types of biomass reactor devices (e.g. different sizes, capabilities), wherein each bioreactor may receive the same, or different types of biomass. Dependent on the implementation, the sensor system 120 may further comprise internal sensors 122 on and within some and/or all bioreactors no, as shown in FIGS. 2-3. Alternatively, the sensor system 120 may comprise a single set of internal sensors 122, as shown in FIG. 4. As part of the network of bioreactors, the system may additionally comprise a single communication unit 130, or a plurality of communication units, wherein each employed communication unit may be associated with a single, or multiple bioreactors no, from the network of reactors. The network of bioreactors may function to enable determination and production of an optimal end-product(s) for the entire network of bioreactors no, or a subset, of the bioreactors; wherein data from the entire network may be leveraged to determine the optimal end-product(s).

Although technically biomass may comprise any plant material (e.g. brush, foliage) or animal material (e.g. carcasses, food waste); the term biomass, as used in this document, is used to characterize generally, any type of organic material that may be converted into a desired end-product. This may include carbonaceous material that did not originate from plant or animal, particularly any other hydrocarbon compound (e.g. synthetically produced organic material, activated carbon, fly ash, and charcoal dust). In some variations, the desired end-product may be a fuel or energy end-product (e.g. biofuel or heat). The type of biomass utilized with the system may vary depending on many factors, e.g. desired implementation, local region version of the biomass, season, weather conditions, etc. For example, the biomass may comprise a solid fruit biomass (e.g. coconut, mango, orange, etc.). In one example, the biomass may comprise agricultural biomass (e.g. rice, wheat, corn, etc.). In another example the biomass may comprise agricultural residues (i.e. leftover material after the harvest of fruits, vegetables, grains, etc.), for example the plant body, leaves, skin, husks, roots, etc. In another example, the biomass may comprise a solid woody biomass (e.g. shrubs, undergrowth). Dependent on the biomass, biomass type, and desired implementation, the biomass may be broken down into heat and/or any number of bioenergy sources (e.g. fertilizer, or activated carbon, etc.).

The end-product may be a processed compound from the biomass. Preferably, the end-product is an energy rich compound (i.e. bio-based product) that is in a form ready to be utilized (i.e. fuel or heat), although the end-product may be any general desired compound. Examples of possible end-products include: fertilizer, biofuel, activated carbon, bio-coal, briquettes, electricity, and heat generation (e.g. from burning the biomass). The end-product may additionally be a material form intended for carbon sequestration. In some variations, the end-product may be a compound that is only partially processed, e.g. a fertilizer base. In these variations, the end-product may be either treated as a final end-product, processed at a later time, or transported/transferred to the appropriate destination for further processing.

The bioreactor 110 functions as a unit that can store and potentially process the biomass into the end-product. Although this application will generally describe a limited number of types of bioreactor devices, the system may generally comprise any desired, appropriately functioning bioreactor 110. As used herein, a bioreactor (or simply reactor) may refer to any device(s) that facilitate the conversion of biomass into the end-product. The biomass reactor described herein will generally be a biomass reactor with one or more sensors and/or one or more apparatuses enabling the alteration of operation (e.g., air flow) of the bioreactor. Examples of possible reactors include: a batch reactor, a stirred tank reactor, a photobioreactor, and a modified kiln with sensors and an air flow pump, a landfill cap, an earth kiln, and a cookstove. In some variations, the bioreactor 110 may comprise a form substantially similar to the biomass reactor as presented in international application WO2018/213474A1, filed on 16 May 2018. In another variation, the bioreactor 110 takes the form of small-scale, process-intensified pyrolysis reactor; wherein liquids (e.g. bio-oil, diesel) and synthesis gas (e.g. hydrogen and methane) are produced from biomass. In another variation, the bioreactor may take the form of a gasifier, wherein solid biomass may be converted to bio-gas. In one variation, the bioreactor may take the form of a dryer, wherein biomaterial is thermally dried to increase their energy content. Particularly in the network variations, the system may include a large range of types of bioreactors 110, which can differ in any, and all, aspects beyond their ability to receive and process biomass.

The bioreactor 110 may be of any desired size, from a small portable bioreactor (e.g. small enough to be transported in the back of a truck), to a factory sized bioreactor (e.g. that can span multiple acres). Dependent on the type, size, and implementation, the bioreactor 110 may have unique features, such as a loading mechanism (e.g. conveyor), unloading mechanism, waste disposal system, etc.

The bioreactor 110 preferably includes a reaction container. The reaction container functions as one, or multiple, chambers that can contain and/or process the biomass. The bioreactor 110 may comprise an open or closed system. That is, the reaction container containing the biomass may be "sealed", or the reaction container may be open to the external environment. In some variations, the bioreactor no may have an open and closed operating mode wherein the reaction chamber can be changed between a closed and an open system.

In some variations, the bioreactor no includes a power system. The power system functions to provide energy for bioreactor and/or other system component function (e.g. to process biomass, utilize sensors, utilize communication system, etc.). This may particularly be the case in more remote region operating conditions, wherein the system components have no access. In some variations, the power system provides an initial net of energy to initiate an energetically favorable reaction, which may then provide energy for bioreactor no operation. This energetically favorable reaction may be conversion of the biomass to the desired end-product. Alternatively, the energetically favored reaction may be an alternate side reaction (e.g. burning biomass to generate heat energy). The power system may, or may not, provide energy throughout the bioreactor no and/or system operation (e.g. through the use of a high energy battery). The power system may be implementation specific and may comprise an energy repository (e.g. battery), generator, or both. The power system may also include, or integrate, with power sources such as a renewable energy power source (e.g. solar power) or other types of sources that can be used to supply energy. In variations that include just a battery power system, the battery preferably has sufficient energy to initiate bioreactor operation/reaction.

In variations, where the bioreactor no implements an energetically favorable reaction to power the system, an energetically favorable reaction may be utilized to charge/recharge the battery. The system may additionally or alternatively couple to an external power system to run system components or charge the bioreactor battery. Example power systems include: a thermoelectric generator, that uses a thermal gradient across the biomass reactor; heat/steam engine, that generates energy from the bioreactor exhaust; wind turbine; or a wave power generator, that generates energy from waves.

In some variations, the bioreactor 110 is a portable bioreactor. The portable bioreactor 110 functions to enable the storage and processing of biomaterial in locations not normally accessible to larger bioreactors. Accordingly, in some implementations, the portable bioreactor may be attached to a form of locomotion so that it can be moved and used in various locations. In some variations, the portable bioreactor 110 comprises a volume 30 to 250 m^3. Preferably, the portable bioreactor no may receive multiple types of biomass (e.g. food trash, wild brush, agricultural residue). The portable bioreactor no may preferably change internal conditions to process the biomass.

The bioreactor may include operation modes such that the conditions of the reaction container can be changed (e.g. to process the biomass). The types of changes that may be dependent on the specific bioreactor 110 and implementation, wherein the bioreactor may include additional one or more system components to implement the conditions (e.g., a condition augmentation system). Examples of potential condition augmentation systems that can be integrated with the reaction container may include: temperature regulator (e.g. by an electric, gas, or other form of heating system), pressure regulator (e.g. using an air compressor), oxygen regulator (e.g. by opening and closing the reaction container, volume regulator (e.g. by having actuating container walls), condensation regulator, chamber agitation system, and/or any suitable system used to alter or control conditions in the reaction container. Additionally, the reaction container may have inlets and/or outlets to add and or remove particular reaction components to the reaction container (e.g. water pump, or waste removal filter). One or more condition augmentation system, such as those described above, is preferably connected directly or indirectly to a control unit 140.

The bioreactor 110 may further leverage changes in the bioreactor no conditions to induce desired processes. Examples include: thermal conversions (e.g. torrefaction) and biochemical conversions (e.g. fermentation). These processes may be implemented by changes in temperature, pressure, and addition and reduction of gas flow (e.g. oxygen) through the bioreactor. In one variation, the bioreactor may produce primarily solid product bio-fuel (e.g. fertilizer base, bio-coal) by decomposing biomass. In another variation, the bioreactor no may produce just energy (e.g. through combustion of the biomass in high oxygen concentrations). In a third variation, the bioreactor no functions in low oxygen conditions (e.g. by closing the reaction container).

The bioreactor no is preferably enabled to function in a processing mode, wherein the bioreactor is enabled to "process" the biomass by changing the internal conditions of the bioreactor. The processing mode functions to produce a desired end-product by inducing physical and chemical changes within biomass. These changes may include intrinsic changes, such as: increasing/decreasing temperature, increasing/decreasing pressure; and/or extrinsic changes, such as: adding/removing biomass material (e.g. separating different biomass components), adding/removing other components (e.g. removing a reaction waste component), increasing/decreasing the rate at which biomass material is added, increasing/decreasing the rate at which other components are added/removed, increasing/decreasing flow of gas/liquid components (e.g. increasing oxygen flow for combustion). In variations wherein the reaction container comprises multiple chambers, the bioreactor 100 the processing mode may move material into different chambers and initiate different processes in these different chambers.

The processing mode functionality of the bioreactor 110 is preferably dependent on the specific implemented biomass reactor, the biomass to be processed, power system of the bioreactor, and the desired end-product. For example, one implemented bioreactor 110 may only be specific to receiving one type of biomass material (e.g. wood) and converting it to one end product (e.g. partial oxidation/gasification of wood to produce syngas). A second implemented bioreactor no may receive multiple types of biomass material (e.g. garbage including paper, wood, food waste) and process them to one end-product (e.g. partial oxidation/gasification of garbage to produce syngas). A third bioreactor 110 may receive multiple types of biomass material (e.g. garbage) and covert it to multiple types of end products (e.g. separating garbage and producing biogas, bio-coal, ethanol, and biodiesel from the components using combustion, torrefaction bio-esterification, and fermentation). A fourth bioreactor no may receive a single type of biomass material (e.g. wood) and covert it to multiple end-products (e.g. solid fuel and heat).

The sensor system 120 functions as a monitor of the biomass environment. The biomass environment preferably includes the interior of the bioreactor no (e.g. reaction container), the exterior of the bioreactor (e.g. outside temperature), and the biomass itself. That is, the sensor system 120 comprises sensor components, wherein sensor components function to acquire/monitor data specific to the bioreactor 110, the biomass, and/or biomass related information (e.g. local weather). As the system can be used in a portable bioreactor, the system can use the sensor system 120 to inform how operation of the biomass reactor should be changed to address the likely conditions of the biomass input and expected operational conditions. Thus, the sensor system 120 may additionally or alternatively include sensor components that acquire/monitor data regarding the exterior of the bioreactor 110, source location of the biomass, and potentially any other desired or pertinent information. Thus, dependent on implementation, the sensor system 120 may comprise internal sensors 122, sensor components employed on or within the bioreactor 110; and external sensors 124, sensor components employed outside and/or away from the bioreactor.

In variations for a network of bioreactors 110, each bioreactor may have a sensor system 120, as shown in FIG. 2 and FIG. 3. Alternatively, as shown in FIG. 4, a single sensor system 120 may monitor all, or a subset, of bioreactors 110. In one implementation, each bioreactor 110 internal sensor components 122 (e.g. pressure gauge within each reaction container), whereas groups of bioreactors utilize a single external sensor component 124. Generally, sensor system 120 components may be allocated as desired. The sensor system 120 may provide information, the bioreactor 110 to assist in bioreactor function (e.g. to aid the bioreactor to correctly process the biomass), and to the control unit 140, to enable the appropriate actions in controlling system components. In some variations, the sensor system 120 may also provide information to an external user(s), as desired.

The sensor system 120 may include internal sensor components 122, comprising at least one sensor on or within the bioreactor 110. Internal sensor components 122 function to monitor the bioreactor 110 and/or the biomass within the bioreactor, prior to, during, or after biomass processing by the bioreactor. Internal sensor components 122 may include: camera sensors (e.g. digital film camera, spectrometer), reactor positioning sensors (e.g. gyroscope), temperature sensors (e.g. thermometer), pressure sensors (e.g. barometric pressure transducers), sample extractor (e.g. for chemical analysis), humidity sensor (e.g. hygrometer), composition sensors (e.g. ultrasound, spectrometer), and/or other suitable types of sensors. The type of sensor used may be dependent on the implementation, preferably dependent on the specific bioreactor 110 and the type(s) of biomass that the bioreactor can process.

The sensor system 120 may include external sensor components 124, comprising at least one sensor employed outside and/or away from the bioreactor. External sensor components 124 function to monitor conditions outside of the bioreactor 110. External sensor information may be leveraged to determine general knowledge regarding the biomass to help determine optimal end-products from the biomass, and to help improve biomass processing. For example, external sensor components 124 may be utilized to determine the season of the year and recent weather condition history which may be used to determine the condition of the biomass. For example, recent weather may help determine the moisture content of the biomass (e.g. how wet woody biomass is). In another example, the external temperature and season may be leveraged to help determine the biomass condition (e.g. rice residues or coconut residues condition may be determined from seasonal data). External sensor components 124 may be positioned directly exterior to the bioreactor 110 or may be within proximity of the bioreactor. For networks of bioreactors 110, external sensor components 124 may be shared between bioreactors 110 that are in sufficient proximity. Examples of external sensors components 124 include: temperature sensors (e.g. thermometer), general weather sensors (e.g. temperature, wind, humidity), altitude, and geolocation. In some variations, external sensor components 124 may further include sensor components involved in soil analysis. These may be particularly useful in regions where biomass material comes from farming regions. In these variations, external sensor components 124 may further include soil extraction tools to analyze soil contents (e.g. micronutrients) and soil pH. Additionally or alternatively, in some variations the system may access external sensor components 124 external to the system. For example, general weather information may be collected and updated from a local weather station.

In variations for a portable bioreactor 110, the external sensor system 124 may include a geo-location device. The geo-location device functions to identify the location of the bioreactor 110 and potentially the surrounding regions. In addition to other uses, geo-location information may be leveraged to help monitor bioreactors 110 and also to determine the type of collected biomass. The geo-location device may be a GPS, an antenna triangulation device, or any other type of device that can identify the location of the bioreactor no. Additionally, the geo-location information may be leveraged to determine the amount/quantity of biomass available in a certain region. This information may be additionally used to determine the method and costs involved in biomass and end-product transportation.

The communication unit 130, may function to enable information exchange within the system between components distant from each other (e.g. over a network of bioreactors) and with external systems and components. The communication unit 130 may thus enable external control of the system, such that the system may be monitored and controlled remotely. Additionally, the communication unit 130 may connect to and communicate with external "information" sources, providing the system with additional "sensor" information. The communication unit 130 may have any desired method of communication, e.g. IR, Bluetooth, Wi-fi, light, radio signal, and wired communication. In network variations of the system, the system may have one, or multiple communication units 130. For example, for variations of the system wherein multiple bioreactors are distant from each other, each bioreactor no may have a single communication unit, as shown in FIG. 3. In the same manner, for a network variation wherein all system components are close and directly connected, a single communication unit 130 may hardwire all bioreactors no and then connect the entire system to external components. In some non-portable variations, the communication unit 130 may comprise a direct external connection (e.g. landline).

The communication unit 130 preferably provides an external data interface. Through the external data interface, the system may acquire desired data from outside of the system, e.g. commodity data regarding end-products, weather data from a weather station, pricing data from a marketplace exchange, etc.

In some variations, the communication unit 130 may enable external control of the system. This is preferably accomplished through a user interface. Through the interface, a user may receive data (e.g. sensor system 120 data, marketplace data, control unit 140 data) from system components and send out commands to the system and/or system components. Additionally, a user may also implement additional data into the system. User control data may include adding additional parameters, modifying control unit 140 operations, adding new control unit operations (prioritizing low carbon emission end-products), and cancelling current operations.

The control unit 140, functions coordinate and control all system components. Additionally, the control unit 140 may function to determine biomass details (e.g. biomass quantity and biomass quality). Additionally, the control unit 140 functions to automatically determine a final end-product that should be produced by the bioreactor no. The control unit 140 may be directly connected to other system components, as seen in FIG. 1 and FIG. 4, but may alternatively be at some other desired location (e.g. at a user residence). In some variations, the control unit 140 may be a processor on some network (e.g. on a network cloud).

In some variations, the control unit 140 determines details regarding the biomass. The level of detail determined by the control unit 140 may differ dependent on implementation and known biomass details. In variations wherein the biomass type is already known, the control unit 140 may use user input data (e.g. biomass type). Alternatively, the control unit may attempt to determine biomass details by matching biomass data obtained from the sensor system 120 with external databases, accessed through the communication unit 130.

Additionally, in some variations, the control unit 140 may be involved in locating and tracking biomass. That is, the control unit 140 can also be used to track the location and quantity of biomass raw materials. This may be done by accessing surveys and GIS databases. In this manner, the system may be able to provide a proof of environmental sustainability, that can use to brand products (e.g. Fair Trade). This could be done by say, using, blockchain technology coupled with our control system network. This functionality may be part of or in tandem with a control unit 140 account management system.

In some variations, the control unit 140 may further be involved in gathering biomass. The control unit 140 could be used to control the process of biomass extraction. In these variations, the control unit 140 may work in tandem with an extracting device (e.g. a rice harvester), wherein the control unit 140 monitors may direct the extracting device to the appropriate locations, and control and monitor the rate at which the harvest gathers and delivers biomass.

In some variations, the control unit 140 determines the final end-product product by the bioreactor(s). That is, the control unit 140 may use sensor data, external data, and bioreactor performance to determine one or more desired end-products. Dependent on implementation, any desired metric may be implemented with the control unit 140 to determine the end-product. In one variation, the control unit 140 may use profit (e.g. the end-product that would return the largest profit margin) to determine the final end-product. In a first example, the control unit 140 determines the biomass quantity and composition, determines the end-products that the bioreactor no may create from the biomass, analyzes the market prices for the end-products, and determines the end-product that the bioreactor should produce. In a second example for a network, the control unit 140 uses the biomass quantity and composition from each bioreactor no, determines the end-products that the bioreactors may create from all the biomass, analyzes market prices for the end-products, and determines the end-products to be produced by each bioreactor. In addition to market prices, the control unit 140 may analyze any and/or all other desired information that may help decide the final end-product (e.g. cost of end-product transportation and cost of end-product production).

In other variations, the control unit 140 may determine the final end-product using other factors, and perform similar maximizing tasks, as per the profit variation, to determine the final end-product. For example, in one variation, the control unit 140 may determine the final end-product by determining the end-product with the smallest carbon footprint. In a single bioreactor example of this variation, the control unit 140 determines the biomass quantity and composition, determines the end-products that the bioreactor 110 may create from the biomass, obtains and analyzes the carbon emission data for the different potential end-products, and determines the end-product that the bioreactor should produce by choosing end-product with the smallest carbon footprint. The control unit 140 may additionally take into account carbon emissions for producing and transporting the end-product. The control unit 140 may be set to determine a final end-product using any desired criteria. Examples include: maximizing direct implementation (e.g. locally used fertilizer), minimizing energy waste, and maximizing fire mitigation, and fastest reaction time.

In some variations, the control unit 140 may control production of the end-product through control of the bioreactor. Once final end-product has been determined, and the reaction required to convert the biomass into the final end-product determined, the control unit 140 may activate and control the process. That is, the control unit 140 may activate and configure the bioreactor for the appropriate reaction process. The control unit 140 may control any and/or all chemical processes for the system.

For example, for a torrefaction process, the control unit 140 may activate the temperature regulator of the bioreactor such that the temperature rises to over 200 degrees Celsius and adjust the oxygen flow rate into and out of the bioreactor to remove all oxygen from the reaction container. As the temperature is increased, vents may be opened to release pressure, such that the chamber pressure is close to atmospheric pressure. During the torrefaction process, the control unit 140 may additionally open drains to enable release moisture lost by the biomass.

In some variations, the control unit 140 may also concurrently, or preemptively "dispose" of the end-product material, e.g. sell the end-product. Particularly for the marketplace variations, but valid in any other variation, the control unit 140 may sell the end-product once it a final end-product has been determined. In addition to the sale of the end-product, the control unit 140 may set up other associated factors, e.g. logistics of end-product transport.

In some variations, the system may include an account management system that is operated in coordination with the control unit wherein operator accounts for one or more biomass reactors can have production tracked and metered. Based on the tracked operation, the operator accounts may be credited. In a preferred variation, this may include initiation of a financial transaction to deliver payment to an account associated with the operator account to pay them for the produced product. In another variation, the operator account may have a set status that enables the use of the control unit such that they can operate their biomass reactor using the system. The status of their account may alter how their biomass reactor can operate. For example, the options for production may be modified based on the status of their account, the amount of an output may be limited, the amount of biomass processed may be limited, and/or other limits may be put into place. For example, an operator account linked to a biomass reactor may pay to have their account to a status allowing up to two tons of biomass to be processed in a given month. The amount of biomass processed is measured, and control directives are supplied for up to two tons biomass during a given month. Other alternative metering and forms of financial arrangements may alternatively be enabled with the system. In some variations, operation of the bioreactor can be remotely controlled based on the status of an account. For example, a bioreactor may be remotely locked, deactivated, and/or otherwise limited based on the status of an account (e.g., failure to pay subscription fee).

3. Method

Figure 5:
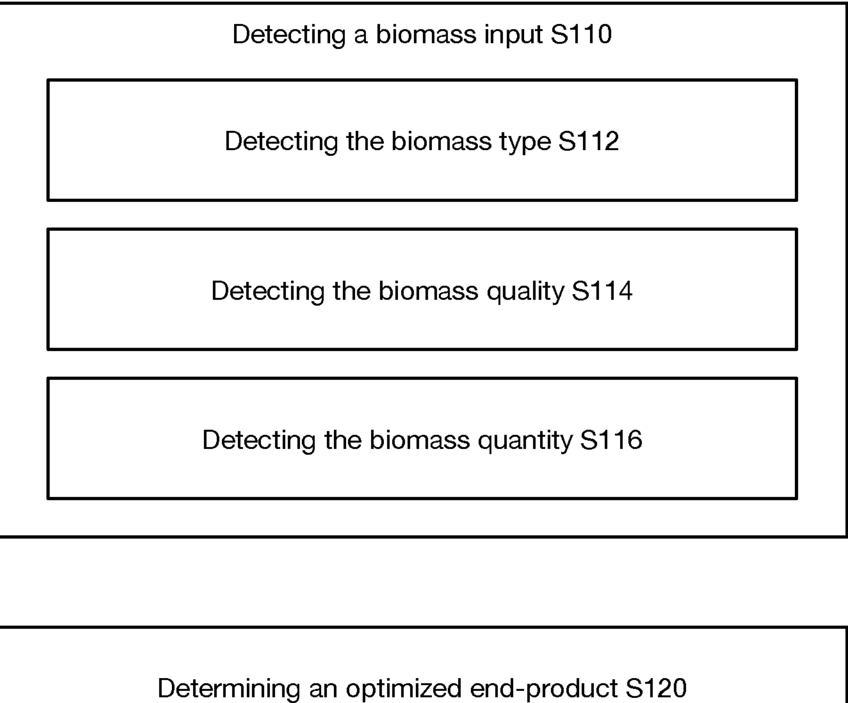
FIG. 5 is a flowchart representation of a first method.

As shown in FIG. 5, a method for a reactor-based biomass processing, includes: at a reactor, detecting a biomass input S110; at a processor, determining an optimized end-product S120, wherein the end-product is at least partially based on: the biomass input, local conditions, and a production target; and at the reactor, producing the end-product S130. The method functions to enable and direct a reactor to produce an optimized output from the biomass, wherein the processor may leverage internal biomass data with external biomass data, with a user input (i.e. a selected production target) to determine the optimized end-product and an optimal method to produce that end-product. That is, the method functions to optimize biomass processing to meet a production target by utilizing internal reactor and biomass data, with external data regarding the location, history, and market information (e.g. market prices, available supply/demand) of the biomass. Thus, detecting a biomass input S110 may further include: detecting the biomass type S112, detecting the biomass quality S114, and detecting the biomass quantity S116.

The method may be further implemented over a network of reactors, such that determining an optimized end-product S120 is dependent on both the input and the potential output of the at least a portion of reactors in the network of reactors. Additionally, in determining an optimized end-product for the network, each biomass input and the local conditions can be unique to each reactor. Implementing the method over a network of reactors may function to provide even more optimized end-products for the entire network. Additionally, the network may potentially set up an end-product exchange, wherein different users may produce end-products optimized for the use of others.

In many variations, detecting a biomass input S110 and determining an optimized end-product S120 may include acquiring external factor data, which can then be correlated with known (i.e. detected) biomass input data. Acquiring external factor data may include interfacing with one or more data inputs (e.g. accessing databases, libraries, and/or other resources, scanning market exchanges, contacting experts, etc.) to detect the biomass input S110, determine an optimized end-product S120, or substeps of either. This can include retrieving and/or otherwise accessing external datasources for information on weather, biomass mapping data, sensor data (e.g., a database of farm soil tests at various locations), and/or any suitable type of data.

Figure 6:
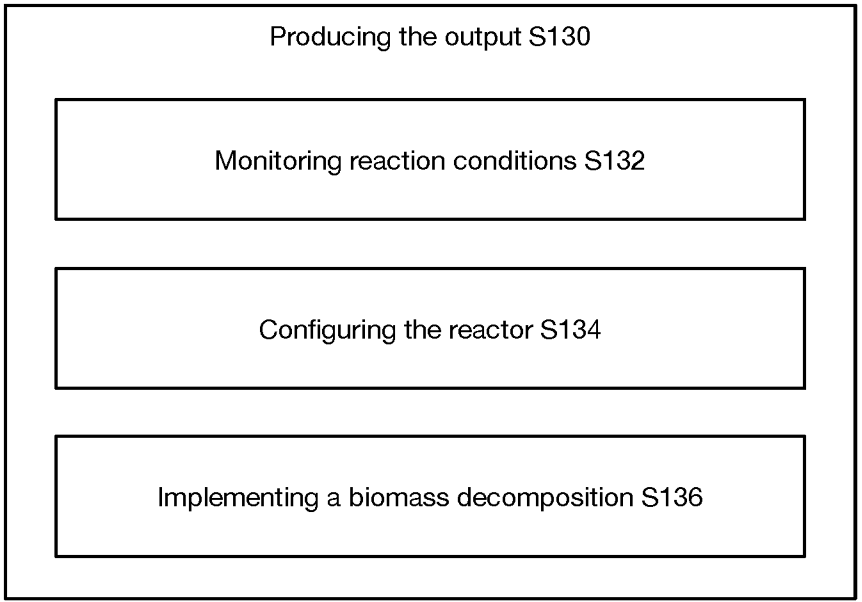
FIG. 6 is a flowchart representation of a variation of a method step.

In many variations, producing the end-product comprises enabling the biomass to undergo the maillard reaction, gasification, or combustion, to produce the end-product. Thus, as shown in FIG. 6, in some variations, producing the end-product S130, may further include: monitoring the reaction conditions S132, configuring the reactor S134, comprising adjusting an oxygen flow rate into the reactor; and implementing a biomass decomposition S134. Adjusting the oxygen flow rate may function as a critical step for biomass decomposition to the desired end-product. For example, torrefaction may occur at high temperatures in the absence of oxygen; while combustion occurs at high temperature with the regular flow of oxygen.

The method may be implemented with a system as presented above but may be implemented with any reactor-based biomass information gathering system and/or biomass processing system. That is, in many implementations, the method may be implemented as part of a computer-readable storage medium (e.g., a non-transitory computer-readable storage medium) comprising computer-readable instructions that, when executed by one or more processors of a machine, cause the machine to perform operations of the method. Accordingly, the method may be implemented in part as "control" software, wherein users may utilize the method (e.g. as a purchased software or software subscription) to input biomass data and receive real-time optimized end-product "suggestions" to be used in conjunction with a biomass reactor as configuration for operation of the biomass reactor. In one implementation, the method may be partially or fully integrated with system components such that the method can control those components (directly or remotely) and actively perform method steps using, or in conjunction with, the system components. In other variations, the method may enable at least partial user interaction such as by supplying input or selection of some operation configuration parameters. The control software implementation of the method may comprise original programming of hardware components, installable programming for hardware components (e.g. upgradable firmware), installable program for a personal computing device (e.g. personal computer, tablet, phone), web service (e.g. website API) or any desired implementation.

The method may enable monitoring, analyzing, and processing biomass remotely. In some variations, the method may be implemented over an electronic interface (e.g. smartphone, or computer) to remotely monitor, determine, and control the production of an optimized output from a biomass input in a reactor. The method may enable control, monitoring, and diagnostics of a single, or a network of reactors through the entire process. In this manner, an entire network of reactors may be customized for an end user's needs as specified through a production target.

The method may be implemented with any level of integration, as desired, thus enabling a functionality related with that level of integration. As presented, no distinction will be made between different implementations and different levels of integrations of the method with system components; such that method steps and substeps may be added, removed, repeated, and/or implemented in different orders as deemed necessary for a given implementation. For example, as per block S110, detecting a biomass input may include: detecting the biomass type S112, detecting the biomass quality S114, and detecting the biomass quantity S116. As an implementation with a particular known biomass of a given quantity, the step may simplify to detecting the biomass quality S114. In another example, multiple types of biomass may be input, wherein block S110 may be performed multiple times to characterize the multiple types of biomass.

Block S110, which includes detecting a biomass input, functions to detect and/or determine pertinent details regarding a biomass input for processing. Determining a biomass input S110 may include detecting the biomass type S112, detecting the biomass quality S114, and detecting the biomass quantity, S114. Detecting a biomass input S110 may be implemented for a single, or multiple, types of biomass, wherein any amount of knowledge about the material may be known or unknown a priori. In variations wherein the biomass input data is known a priori, detecting a biomass input S110 may be implemented to verify "known" information and/or monitor changes to the biomass input properties.

In many variations, detecting a biomass input S110, and its substeps, comprise using sensors to analyze the biomass input. In many variations, these sensors comprise sensors, or other measuring devices, on bioreactors that are used to analyze biomass once input into the reactor. Additionally or alternatively, external sensors may be used to analyze the biomass input. For example, collected foliage to be used as biomass input may be initially weighed during truck transport to a bioreactor. Examples of reactor sensors may include: temperature gauge (e.g. thermometer), camera sensors, scale, pressure gauge (e.g. barometer), a sample extractor (e.g. for chemical analysis), humidity gauge (e.g. hygrometer), and composition sensors (e.g. ultrasound, spectrometer). Other sensor components may be implemented as desired. Accordingly, the detecting biomass input S110 may include analyzing the biomass input by collecting temperature data from a temperature gauge, collecting image data of the biomass input from a camera/imaging sensor, measuring weight, measuring pressure, performing a chemical analysis of the biomass input, measuring humidity, analyzing biomass input composition, and/or performing other forms of analysis of sensor input.

As part of detecting biomass input S110, sensor data may be compared and/or correlated with information databases and/or repositories (e.g. material property databases, geographic information system (GIS) frameworks, regional maps, location history databases, weather station data, marketplace prices, etc.). In these variations, detecting the biomass input S110 may leverage information from previously known information databases with obtained sensor data to correlate biomass input properties. Additionally, as part of the method, when applicable, these databases may be updated to incorporate newly obtained information from method steps. In one preferred variation, the method further includes creating and updating an information database. In this variation, the method may create an information database that includes any and/or all data obtained through the method. Examples of information stored in the database may include: time-based biomass compositions (i.e. seasonal changes in biomass quality), regional-based biomass compositions (i.e. trends in biomass composition dependent on region), weather-based biomass composition (i.e. weather based trend correlations in biomass composition), etc. In some implementations, machine learning (e.g. reinforced learning) may be incorporated with the database to optimize biomass input determination. In this manner later iterations of the method implementation, with the stored data may be accessed and used to improve biomass input detection.

The method functions in identifying and processing biomass for typically energy production, either for direct utilization (e.g. heat production or for efficient energy storage (e.g. as a concentrated biofuel). In some variations, the method may be implemented for identifying and processing biomass for other functions, such as waste disposal or fire management. In other variations, the method may function in identifying and processing biomass that is fossil based raw materials. In these variations, the method may bring about energy efficient improvements to existing methods of production (e.g., energy savings in the production of graphite). The types of biomass input may comprise a single type of biomass, or multiple types of biomass, either separated or mixed (e.g. garbage). Thus, the biomass input may include receiving multiple types of biomass concurrently or separately. Biomass input may be a continuous process with "constant" addition of biomass or may occur in discrete elements. This "rate" of biomass input may be dependent on the type and/or method of biomass acquisition but may alternatively be independent of those factors.

The types of biomass received may vary dependent on many factors. Although technically biomass may comprise any plant material (e.g. brush, foliage) or animal material (e.g. carcasses, food waste), biomass here may be used to refer to any organic material that may be converted into a desired end-product preferably an energy end-product. For example, petroleum coke or coal. In some variations, biomass input may include non-usable material (e.g. as part of garbage collection). In these variations, the method may further include steps for removing and/or disposing of non-usable material. Alternatively, the non-usable material may be allowed to go through the entire process (particularly if it has little to no effect on other method steps) and be present in the final end-product. Examples of biomass material include: vegetation material (e.g. brush, foliage), vegetation waste/residues (e.g. coconut residues, rice residues), animal material (e.g. carcasses), animal waste (e.g. guano), synthetically produced organic material (e.g. activated carbon, fly ash, and charcoal dust), and/or other biomass materials.

Block S112, which includes detecting a biomass type may be a component of the detecting a biomass input S110. Detecting a biomass type S112 may function to detect and/or determine what the biomass input is. Detecting the biomass type S112 may include using sensors to identify the biomass, receiving a user input that identifies the biomass, or some combination of both. For example, in one combination implementation, identifying the biomass may include a user identifying the biomass as an "unknown" garbage, and sensors identifying some and/or all types of biomass contained within the garbage (e.g. plant material, unusable trash, feed).

In some variations detecting the biomass type S112 may comprise sensors identifying the biomass input. Sensors identifying the biomass input may be implementation dependent and potentially limited by the resources made available at/through the reactor that receives the biomass input. Sensors identifying the biomass input may comprise one, or more, sensors evaluating the biomass input which then may be correlated with known databases of material properties. Identifying the biomass input through sensor data input generally involves collecting sensor data from one or more sensor data and processing the sensor data to determine at least one property of the biomass input. In some cases, the sensor data may be used to classify the type of biomass input. In cases where there is a mixture of biomass materials supplied as an input classification of multiple types of input may be made. In some cases, this may include estimating proportions of different types of biomass materials in the biomass input. Determining a property of the biomass input may additionally be used in classifying and/or measuring other properties such as estimated quantity, expected moisture content or other properties.

In one example, a camera is used to evaluate the biomass input wherein the method includes collecting image data and analyzing the image data of the biomass input. Images of the biomass input may be analyzed through a general image search, computer vision processing (e.g., classifying through neural network classifier model), and/or using any type of image data analysis process. In another example, spectrometric analysis of the material may be compared to databases to determine the material properties of the biomass. Multiple correlations may also be used to determine the biomass. In another example, wherein the sensors comprise a scale and a camera, image analysis may help determine a unit volume for the biomass input, and the scale may provide a unit weight for the biomass input. Determining the unit volume from image data can include estimating volume of the biomass input from the image data (e.g., generating a depth map from one or more imaging devices). Detecting the biomass type S112 may then comprise correlating the unit density of the biomass input with density databases. Thus a single, or any number of sensors may be used to measure and then compare biomass input data to known databases.

Block S114, which includes detecting the biomass quality may be a component of the detecting a biomass input S110. Detecting the biomass quality S114 functions to determine a more detailed composition of the biomass, wherein this information may be used to improve reactor configurations for better biomass processing. In addition to biomass composition, detecting the biomass quality S114 may also detect other general properties regarding the biomass. Examples of general properties include: detecting changes/variations to the biomass (e.g. if the biomass components or cut into pieces), biomass processing (e.g. separation of fruits/grains from the shell/skin), or biomass chemically or physically altered (e.g. dried skins, animal or vegetation, biomass homogenized).

In some variations, detecting the biomass input includes identifying general properties of the biomass in addition to or as an alternative to identifying a biomass type. These general properties may, for example, identify types of processes/reactions that the biomass can undergo. Examples include: combustibility, gasification, fermentation, torrefaction, esterification, etc. Detecting the biomass quality S114 may comprise using sensors, as described above, to determine the physical properties of the biomass input. Determining the biomass quality S124 may additionally go through iterations, particularly in cases where the biomass input has a complex heterogeneous composition. Detecting the biomass quality S114 may thus comprise detecting small subcomponents of the biomass input, wherein initially a process/reaction for the biomass input is identified. Block S114 may then be repeated to identify the composition of the subcomponent and then additional subcomponents may be identified until the biomass is identified.

In variations wherein the biomass type has been identified, detecting the biomass quality S114 may provide a more detailed assessment of the biomass composition and quality. A detailed assessment of the biomass composition may enable an improved implementation of biomass processing. For example, in an agricultural setting where coconuts are harvested. Coconut residue (e.g. coconut husks, tree material, leaves, etc.) may be comprise the biomass input. For an identified coconut residue biomass input, detecting the biomass quality S114, may comprise determining the moisture content of the residue, wherein the moisture content may be leveraged to adjust reaction temperature and oxygen content of a bioreactor. In addition to analyzing sensor data to determine the biomass composition, for a known biomass type, detecting the biomass quality S114 may comprise identifying regional and seasonal trends for the biomass. As part of the coconut residue example, block S114 may comprise obtaining local history information from where and when the coconut residue was obtained. For example, coconut residue gathered in the summertime may contain less moisture as compared to coconut residue collected in the spring. Additionally, coconut residue from a specific region may have unique structure elements, such as one region coconuts may have a more dense fibrous structure that is harder to burn.

Block S116, which includes detecting the biomass quantity may be a component of the detecting a biomass input S110. Detecting the biomass quantity S116 functions to provide information about the amount of each biomass material, and the rate at which reactors are filled with biomass material. Determining the quantity of the biomass may be determined by sensors, through user input, through external databases, through GIS data, or some combination of methods. In some examples, the exact amount of biomass material may not be easily discernible (e.g. combustible brush from a forest). Dependent on the implementation, determining the quantity of the biomass may include: determining a minimum quantity of biomass, determining an approximation quantity of the biomass, determining a quantity range of the biomass, or leaving the quantity of the biomass unresolved.

In variations where detecting a biomass input S110 is a continuous process, detecting the biomass quantity S116 may be determining the rate of biomass addition. That is, biomass quantity may be detected as a rate of addition (e.g. to a bioreactor). In some variations, detecting the biomass quantity S116 may be additionally or alternatively determined as the rate of biomass addition to a reactor, as compared to the capacity the reactor. Thus, detecting the biomass quantity Sn6 may enable monitoring of a reactor and the potential available capacity of the reactor.

Block S120, which includes determining an optimized end product, functions to determine a relatively optimal end-product for the biomass input, i.e. what the method should produce. Furthermore, S120 may include determining control configuration of a biomass reactor (based on the determined optimal end-product). In many preferred variations, the optimized end-product is at least partially dependent on a selected production target, on the biomass input, and on local conditions. Generally, the optimized end-product may be of any type of end-product. As part of biomass processing, the optimized end-product is preferably an energy rich output that may then be used directly, stored for later energy consumption, and/or sold. Examples of possible end-products include: fertilizer, a fertilizer base, biofuel, activated carbon, bio-coal, briquettes, electricity, and heat generation (e.g. from burning the biomass). The end-product may additionally be a material form intended for carbon sequestration. In some variations, the end-product may be a compound that is only partially processed, e.g. petroleum or coke. In these variations, the end-product may be either treated as a final end-product or transported/transferred to another bioreactor for further processing.

Herein, optimal, or optimized, may be generally used to refer to an enhancement of utility. This enhancement of utility may be for one particular biomass reactor and its operator but may additionally or alternatively refer to an enhancement of utility for a biomass reaction across a number of different entities (e.g., suppliers of biomass, operators of biomass reactors, consumers of biomass reaction products, and/or other entities). Optimal/optimized should not be taken as an absolute, or a local maximum, but as a general improvement over some implemented metric for some preferred or recommended task. In the same thread, the terms maximizing and minimizing are used herein to refer to approaching an enhancement of utility, without the necessity to reaching any type maxima or minima.

Figure 7:
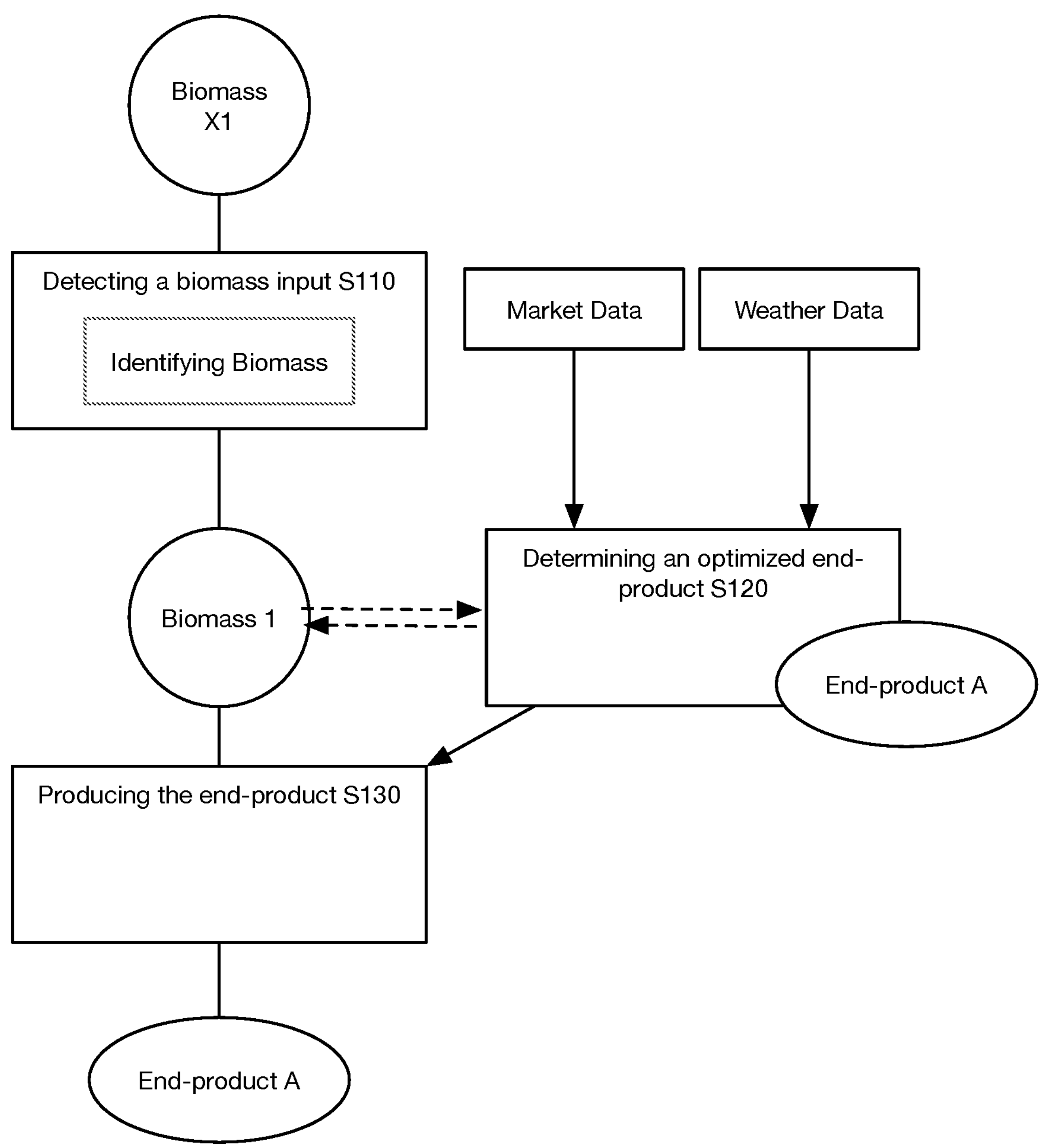
FIG. 7 is a flowchart representation of a first implementation of the method.
Figure 8:
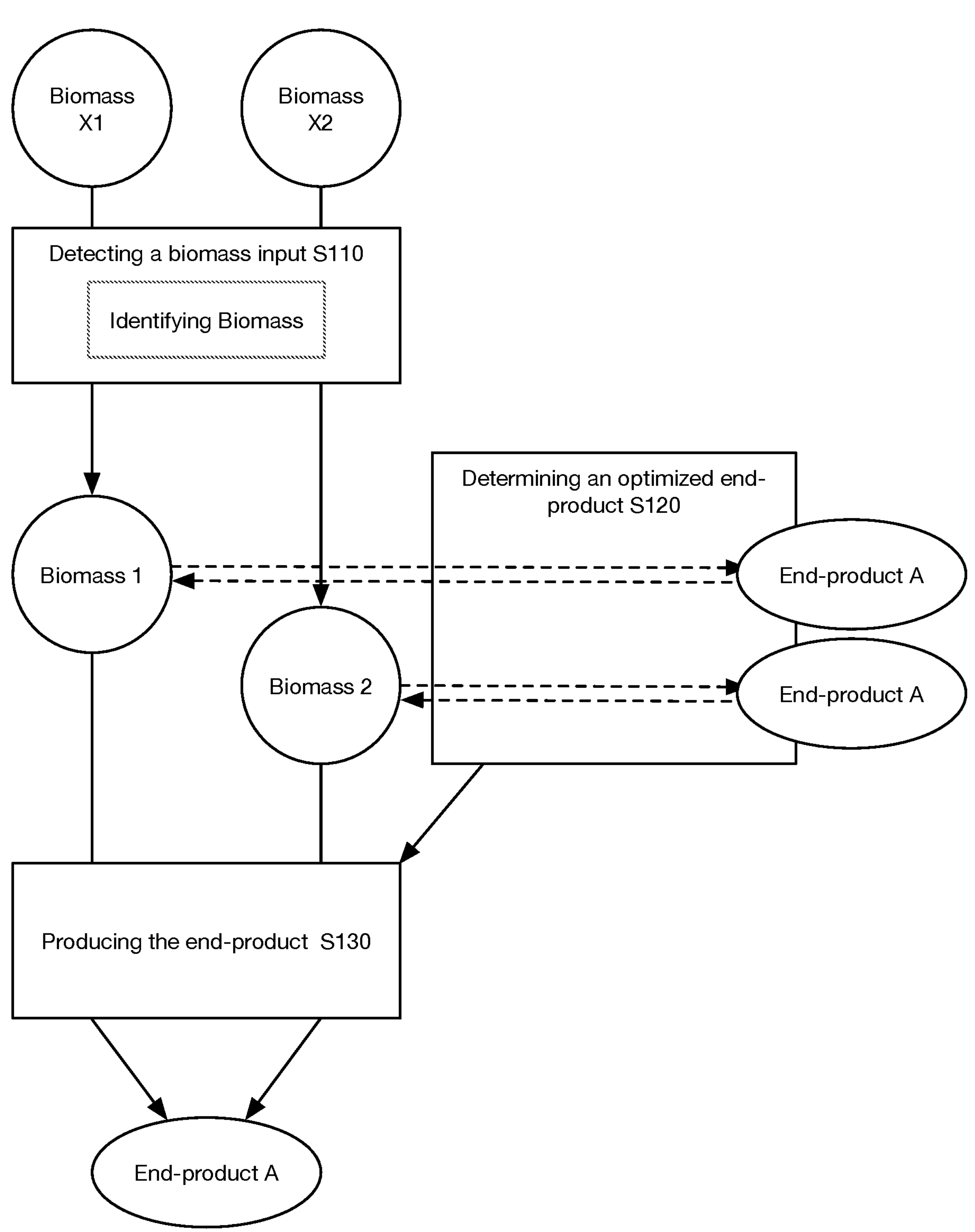
FIG. 8 is a flowchart representation of a network implementation of the method.
Figure 9:
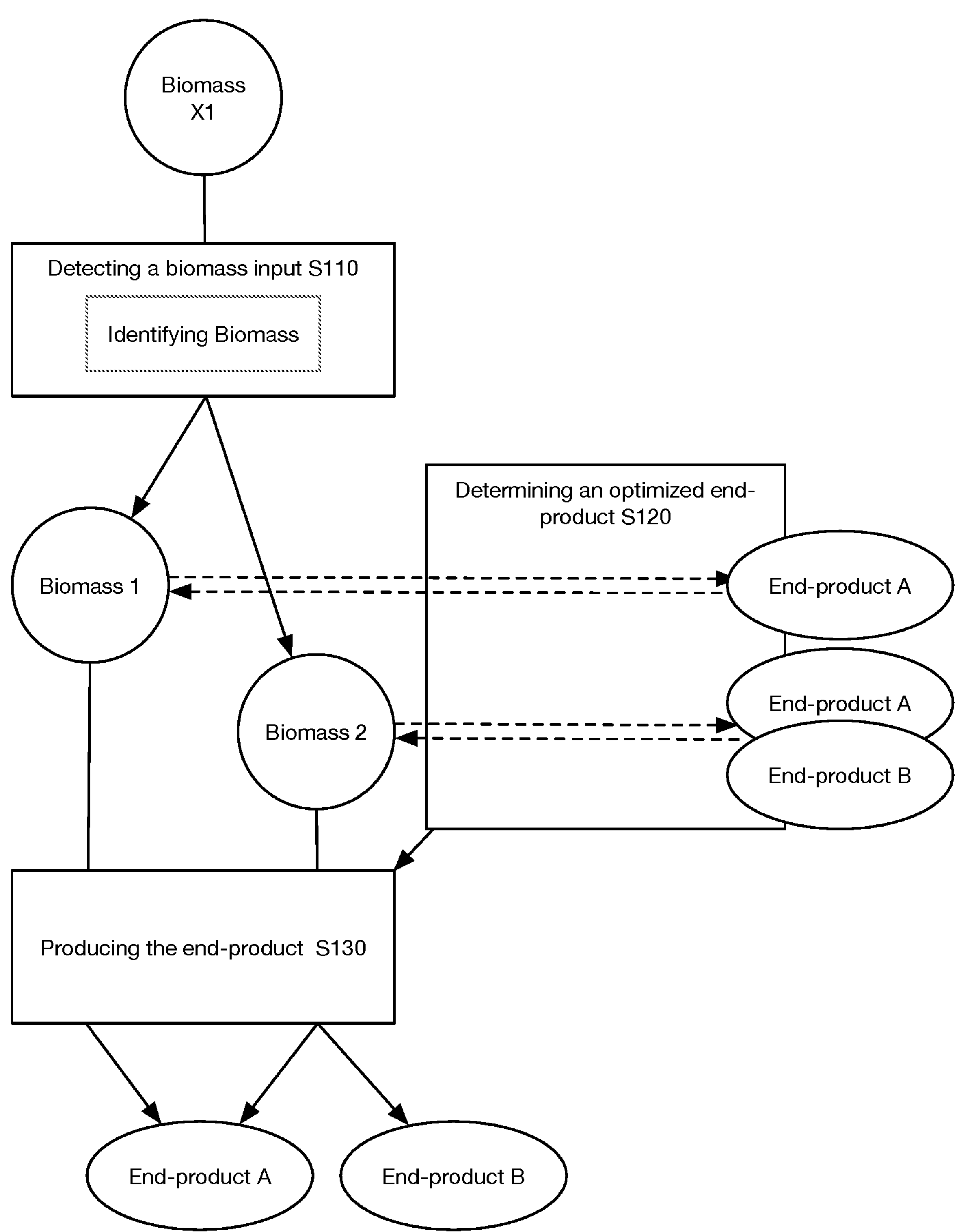
FIG. 9 is a second flowchart representation of a network implementation of the method.
Figure 10:
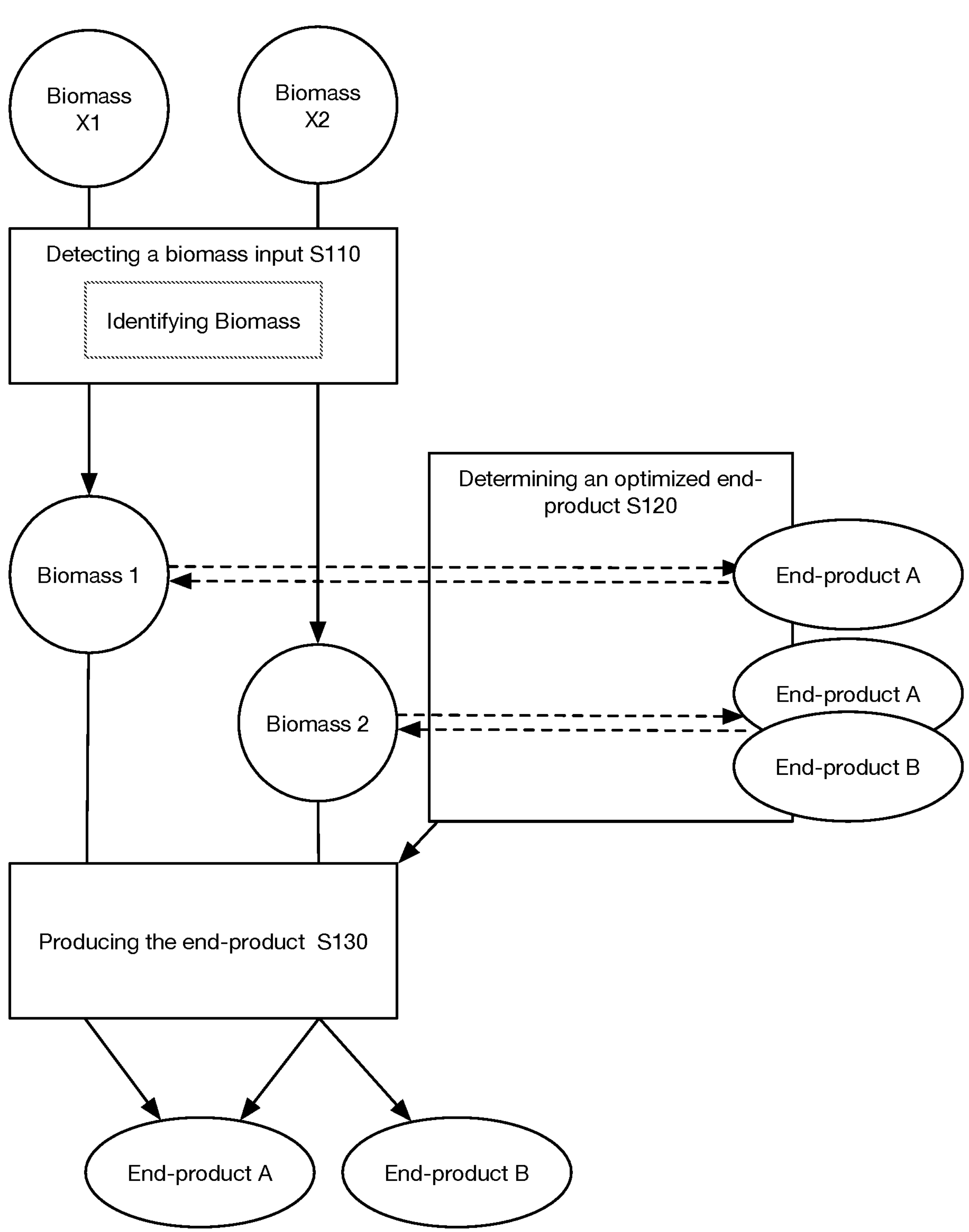
FIG. 10 is a second flowchart representation of a network implementation of the method.

In many preferred variations, the optimized end-product is at least partially dependent on the selected production target (e.g. best market price for the end-product or utilitarian purpose), biomass input, and local conditions. FIG. 7 and FIG. 8 shows a schematic flowchart for determining and producing an optimized end-product. In some preferred variations, determining an optimized end-product S120 may determine multiple optimized end-products, as shown in FIG. 9. This may particularly be the case for implementation of the method with multiple biomass inputs and/or biomass reactors as shown in FIG. 10. Determining an optimized end-product S120 may occur in real-time, thus the end-product can and may change over time. Accordingly, the method can include periodically (or continuously) modifying operation of a biomass reactor in response to updating determination of an optimized end product. For example, if woody biomass is being supplied as biomass input but the moisture levels change overtime depending on the source of the woody biomass.

Determining an optimized end-product S120 may be dependent on several intrinsic and extrinsic factors, wherein some factors are required (e.g. due to physical laws and available technology), while others are non-required factors. As the end-product is dependent on converting some biomaterial into an end-product, there are some factors that may be required. Required factors preferably include: the biomass input and possible end-products that may be produced by the biomass, the biomass reactor type and the end-products that can be produced using the biomass reactor. General factors may include: biomass input type; biomass quality, e.g. size, condition, whole or in pieces, moisture content, pH; biomass quantity; reactor location; weather conditions; biomass reactor efficiency; reactor size; size of input; reactor “traffic” (i.e. rate at which reactor is loaded with biomass); size of potential output; output rate, output properties e.g. cost, energy density, chemical composition (e.g. fixed carbon), volatility, output state (e.g. gas, liquid), output size; reaction cost, and reaction rate. Additional required and non-required factors may be included as production target metrics and/or necessary. In preferred variations, block S120 may enable a user to add, remove, and/or modify these factors (e.g. adding quantity of required reagents to produce an end-product). In this manner, cost (e.g. market price for the end-product) may be included as a production target.

In some variations, the production target may be used to set an end-product, or type of end-product, such that the end-product is not directly sourced from the biomass input. That is, the biomass input cannot be converted to the output. In these variations, block S120 may designate the biomass input to be used as thermal energy (e.g. through combustion). This energy may then be used, wholly or partially, as part of another reaction to create the end-product.

In some variations, determining an optimized end-product S120 may comprise maximizing a cost/benefit analysis for all end-products that can be produced from the acquired biomass. In these variations, the Block S120 may comprise accessing marketplace(s) to determine the current price of each potential end-product. Additionally, or alternatively, any and/or all other factors that may play a role in maximizing a cost/benefit analysis may be accessed or used. Examples of possible factors include: end-product production cost and end-product transport cost (e.g. transportation network optimization, and one end-product may need to be transported further to reach a desired marketplace or is more costly to transport).

In some variations, block S120 may also implement and/or access cost/benefit models, thereby using “future” costs and prices in determining the optimized end-product. Particularly in these variations, but also in other variations, a real-time maximum benefit end-product may include the biomass itself. That is, the optimized end-product may be the unprocessed biomass; storing the biomass until market prices for other end-products rise sufficiently. In this example, determining an optimized end-product S120 may also take into account the storage cost and/or deterioration cost of the biomass. Cost/benefit models may include statistical regressions, AI learning models, trend analysis, and any other type of statistical analysis or desired modeling. Accordingly, in some variations, block S120 can include accessing market or commodity data, analyzing biomass output demand metrics to thereby determine an optimized end product. This can function to adjust biomass output based on current market demands. When implemented within a network of biomass reactors, block S120 may include accessing biomass output data of other biomass reactors and determining optimized end product according to grouped production of biomass outputs across the network of biomass reactors. In some instances this may specifically analyze biomass reactors within a geographic region to the biomass reactor of interest (the one for which the optimized end product is being determined).

Alternatively, determining an optimized end-product S120 may be maximizing/minimizing something other than cost/benefit. Examples that could determine an optimized end-product S120 include minimizing waste, maximizing end-product usage, minimizing carbon emissions, maximizing fire prevention. In all these variations, the method may seek and access external resources, create databases and models to maintain and analyze all necessary data, and perform simulations to determine possible future outcomes. In some preferred variations, determining an optimized end-product S120 can be set to meet a personal need; wherein parameters and weights given to the benefit of end-products may be personalized to any degree desired. In some variations multiple goals may be combined when determining maximum benefit end-product S120.

In addition to, or as an alternative to a market need, location data, climate data, commodity data, environmental data, good manufacturing and production data, trade data, and/or other suitable external data inputs may be collected and incorporated into predicting a measure of utility for various options. In another example, for a group of farmers that have a need for fertilizer, determining an optimized end-product S120 may comprise first determining the type (s) of fertilizer that may be produced from the biomass input. Block S120 may further include: analyzing regional location data to determine soil conditions, climate data to determine general weather patterns, and request information regarding the potential crop that may be grown there. The method may then determine an optimal type of fertilizer end-product to produce from the biomass input dependent on the regional soil, seasonal weather conditions, and crop types. In some variations, the fertilizer produced may not be the final end-product. In these variations, the fertilizer produced here may serve as a fertilizer base, which could then would be processed to final desired fertilizer output.

In another variation, the optimized end-product may also depend on the power source implemented with the bioreactor. For example, in more isolated regions, the cost of energy may be higher (e.g. due to transportation), and thus an initiating a reaction with a higher activation energy may not be optimal. In another example, the amount of energy or the energy regeneration (e.g., via solar) may limit the types of processes that can be implemented.

In some variations, determining an optimized end-product S120 further includes allocating the end-product. Allocating the end-product functions to commit the end-product to a final use. Allocating the end-product may function differently dependent on how the desired end-product was determined. In the variation for maximizing cost/benefit to determine the maximum benefit end-product, allocating the end-product may include selling the end-product. Selling the end-product may occur in the same fashion, and at the same marketplaces that were used to determine the selling end-product selling prices. Alternatively, other selling venues may be utilized. In another variation, for maximum local utility, allocating the end-product may include determining and purchasing logistical support to transport the end-product (e.g.

hiring/allocating trucks to transport fertilizer). Preferably allocating the end-product occurs in succession after determining the end-product. Alternatively, allocating the end-product may occur at some later time (e.g. after producing the end-product from the biomass S130).

In some variations, determining an optimized end product S120 may further include setting reactor operation configuration and communicating the reactor operation configuration to the biomass reactor. The reactor operation configuration may define various operating parameters and/or operational functions or sequences of a biomass reactor. In some variations, the determination of an optimized end product may be performed through a remote server in which case the reactor operation configuration may be communicated wirelessly or through a wired connection to the biomass reactor. In some variations, configuration file may be generated which can be downloaded and transferred to the biomass reactor. In other variations, the determination of an optimized end product may be performed substantially on a process at the biomass reactor.

Block S130, which includes producing the end-product from the biomass, functions to produce the end-product. In some variations, producing the end-product S130 produces the optimized end-product or end-products, as determined from block S120. Producing the end-product S130, preferably includes monitoring reaction conditions S132 and configuring the reactor S134 for the output production. In some variations, producing the end-product S130 further comprises implementing a biomass decomposition S136, thereby using the biomass energy to heat the reactor.

In many variations, producing the end-product S130, includes monitoring reaction conditions S132. Monitoring reaction conditions S132 may occur prior to and during processing the biomass. Monitoring reaction conditions S132 may function to observe reaction conditions that may, or may not, be specific to an individual reactor. Monitoring reaction conditions S132 may occur in conjunction and/or in complement to both detecting a biomass input S110 and determining a processing output S120. That is, monitoring reaction conditions S132 may include using reactor sensors to "observe" reactor activity, which in conjunction with biomass input data, optimal output data, may be used for configuring the reactor.

Monitoring reaction conditions S132 may occur concurrent to reactor operation. That is, monitoring the reaction conditions S132 may provide data used to help "control" the reactor activity during biomass processing. Additionally, monitoring the reaction conditions S132 may aid in detecting faults within the bioreactor. That is, monitoring reaction conditions S132 may "observe" malfunction, and/or deterioration of the bioreactor, and potentially providing notifications for necessary and recommended maintenance tasks. This may lead to prediction of impending failure of certain components, enabling repairs or adjustments to be made pre-emptively. Dependent on the type of failure mode, recommendations for maintenance tasks may include: running any range of activity from resetting system compoonent, emptying the reactor, replacing or fixing particular system components, and/or any other necessary action. Detection of malfunction or deterioration may additionally lead to changing the operation of the bioreactor (to reduce damage) until repairs or adjustments have been made.

Block S134, which includes configuring the reactor, is preferably a component of producing the end-product S130.

Configuring the reactor S134, functions to modify the reactor environment to produce the optimized output. Configuring the reactor S134 may work in real time, wherein reactor conditions may be regularly updated in response to response from monitoring the reactor conditions S132. Although in some variations, configuring the reactor S134 may function over a network of reactors, in preferred variations, reaction conditions are configured independently for each individual reactor.

Configuring the reactor S134 may comprise adjusting any and/or all intrinsic and extrinsic variables for optimal production. This may include: adding/removing reactive reagents, heating/cooling the reactor, adding/removing oxygen, initializing/ending reactions, adding/removing biomass from the biomass reactor, increasing/decreasing pressure, and/or any other required process/step to make the desired end-product. In some preferred variations, configuring the end-product S134 comprises at least adjusting the oxygen flow rate, which may enable many types of biomass reactions (e.g. reduce oxygen for torrefaction, increase oxygen flow for combustion). In some variations, configuring the reactor S134 may comprise multiple configuration steps to enable multi-step reactions (e.g. gasification).

In preferred variations, block S134 leverages local history information, with precise biomass input information to better process the biomass in producing the end-product. For example, configuring the reactor S134 may adjust the oxygen flow rate and reactor temperature to take into account the moisture content of the biomass.

In some variations, one optimized end-product is direct energy output (e.g. heat energy). In these variations, producing the end-product S130 comprises implementing a biomass decomposition, thereby converting the biomass to heat. Dependent on the implementation, the reactor may be connected to some type of storage unit, such that the energy may be conserved for later use, or to transfer to some location. For example, the reactor maybe coupled to a steam turbine, enabling conversion of the heat to transferable electrical energy.

In another variation, a solid "intermediate" end-product is used as a stored form of energy. In this variation, producing the end-product S130 comprises implementing a biomass decomposition, such that energy of the biomass is concentrated (e.g. thermal drying). The concentrated form may then be stored until needed (e.g. peek energy demand). Once needed, the concentrated form may then be transported to that location, or block S130 may further process the biomass into usable energy form (e.g. heat).

In many variations, producing the end-product S130 may produce multiple end-products. These multiple end-products may be any combination of end-products discussed herein or some combination of different end-products. For example, in one implementation of coconut residue harvesting, block S130 may produce both an activated Carbon (e.g. coal) end-product and a direct energy end-product (e.g. heat).

In some variations, the desired/optimized output is a compound that may not be produced from the biomass input directly. In one variation that includes biodecomposition, the released biomass energy may be coupled to a second reaction to produce the optimized output. For example, biomass decomposition may at least partially convert the biomass into heat energy (e.g. through combustion). The heat energy production may then be coupled to a second reaction, thereby converting the unchanged biomass, or another compound, into the optimized end product by using the heat energy.

The method may be adapted to many specific uses for managing and controlling mobile biomass reactors and/or networks of biomass reactors used in concert. Three exemplary use cases of method implementations are presented below. In a first example, the method may be implemented by small scale farmers, wherein crop is grown and utilized by the farmers and the leftover over biomass from the crop is utilized as biomass input. In this implementation, farmers grow coconut fruit which is used by the farmers, and the coconut-based residues (e.g. coconut husks) are used as biomass input for the method implementation, wherein the production targeted end-product is solid or gas energy.

In this implementation, detecting the biomass input S110 comprises detecting the coconut residue quality and quantity. For each farmer, detecting the biomass quality S114 may determine the husk sizes and the condition of the coconut husks (e.g. are they whole, cut into shreds, etc.). General local Location, weather, history data may then be used with husk analysis to determine other properties of the husk (e.g. moisture content, presence of minerals, etc.).

Determining an optimized end-product S120 may then leverage coconut residue information, with the farmer's desired type of end-product (e.g. solid or gas energy) to determine an optimized end-product. The optimized end-product may be dependent on the user needs/targets/objectives, the specific residue condition and quantity that the user currently has and the type and size of the farmer's reactor; in addition to potential external factors, such as local conditions, market price of the solid or gas energy (if the user wishes to sell the end-product), and potentially other factors. Using these factors, block S120 may then determine one or more optimized end products that the farmer may produce. In some variations, block S120 may work over a network, such that the data for a network of farmers may be incorporated to determine the optimal end-product for each user. Since a network of users are incorporated, block S120 may take into account particularly the total output size of all groups to determine optimal and future costs of biomass processing and end-product production.

Once the optimized end-product has been determined, block S130 may then automatically configure the farmer reactor to produce the end-product. As each farmer may have different reactors and/or variances in the biomass residues, each reactor for each farmer may be distinctly configured for optimal performance with minimal waste and good quality desired output.

In a second example, the method may be implemented by small scale farmers, wherein crop is grown and utilized by the farmers and the leftover over biomass residue from the crop is utilized as biomass input. In this implementation, farmers grow rice crop, which is harvested and used, and wherein the rice residues (e.g. roots, stems, leaves) are used as biomass input for the method implementation, wherein the production targeted end-product is fertilizer, or fertilizer base, for local farming.

In this implementation, detecting the biomass input S110 comprises detecting the rice residue quality and quantity. For each farmer, detecting the biomass quality S114 may determine the residue sizes and the condition. General local location, weather, history data may then be used for rice residue analysis to determine other properties of the residue (e.g. moisture content, presence of minerals, etc.).

Determining an optimized end-product 120 may then leverage residue information, with the farmer's desired type of end-product (i.e. fertilizer) to determine an optimized end-product. Determining an optimized end-product may then be at least partially dependent on the user needs (e.g.

type of crop that will be grown with the fertilizer), the specific residue condition, the quantity of rice residues that the user currently has, and the type and size of the farmer's reactor; in addition to external factors, such as local soil conditions, current weather, current season, and potentially other factors. Using these factors, block S120 may then determine one or more optimized end products that the farmer may produce. That is, block S120 may determine an optimized fertilizer for the farmer. In some variations, block S120 may work over a network, such that the data for a network of farmers may be incorporated to determine the optimal end-product for each user. In this case, farmers may be able to produce fertilizer that is better and more efficient for a different farmer. The method may take into account cost of travel and exchange and make optimized end products that could then be exchanged with other farmers. In some implementations, the fertilizer produced may serve as a fertilizer base that requires further processing. The method may further take into account the costs associated with the further processing of the fertilizer.

Once the optimized end-product has been determined, block S130 may then automatically configure the farmer reactor to produce the end-product. As each farmer may have different reactors and/or variances in the residues, each reactor for each farmer may be distinctly configured for optimal performance with minimal waste and good quality desired output. Additionally, as weather patterns, crop types, and seasons change, the configuration of the reactor may be adjusted to better take into account new conditions.

In a third example, the method may be implemented for an unknown solid biomass for biomass clearing (e.g. for wildfire management). This use case may be implemented by individual users, fire-fighters, or other interested users. In this use case a generally unknown woody biomass (e.g. brush, foliage) comprises the biomass input, with no specific desired end-product.

In this implementation, detecting the biomass input S110 comprises detecting a multitude of biomass types, in addition to the biomass quality and quantity. As the woody biomass is gathered, general properties of the biomass may be learned (e.g. general composition, density, weight, temperature of combustion, moisture content). These information may be correlated with external databases to determine the specific type of biomass. Additionally, this information may also be added into a database, such that if the biomass type is currently unknown, over multiple iterations the type may be better identified. Thus in preferred variations, detecting the biomass input may be a "remembered" process, such that details regarding the biomass input improve over iterations. Database information may be further improved by correlating the biomass to general local location, weather, and history data. In many variations, woody biomass may in fact comprise multiple different types of biomasses. These may be detected initially, or average properties of some heterogeneous biomass may be used. Over multiple iterations, and reinforced learning models with end-product processing may further enable determining better details for the woody biomass.

Determining an optimized end-product 120 may then leverage all the known woody biomass information, with the to determine an optimized end-product. The optimized end-product may be dependent on local factors, such as the woody biomass composition and quantity, potential end-products, and the type and size of reactor; in addition to potential external factors, such as: local conditions, market price of the end-product, reaction time, rate of loading the reactor, and potentially other factors. Using these factors, block S120 may then determine one or more optimized end products. In some variations, block S120 may work over a network, such that the data may be shared and optimized for all users, and thereby incorporating all user biomass and potential end-products to determine the optimal end-product for each user. Since a network of users are incorporated, block S120 may take into account particularly the total output size of all groups to determine optimal and future costs of biomass processing and end-product production. As part of wildfire management, the rate of reaction may be sometimes imperative, as the priority of this implementation may be to dispose of combustible woody biomass. In this example, the optimized end-product may be significantly different in different regions dependent on the desired urgency.

Once the optimized end-product has been determined, block S130 may then automatically configure the reactor to produce the end-product. As each user may have a different reactor and the woody biomass collected by one user may differ significantly from another user, each reactor for each user may be distinctly configured for optimal performance with minimal waste.

4. System Architecture

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, but any suitable dedicated hardware device can (alternatively or additionally) execute the instructions.

In one variation, a system comprising of one or more computer-readable mediums storing instructions that, when executed by the one or more computer processors, cause a computing platform to perform operations comprising those of the system or method described herein such as: receiving a biomass input; determining a maximum benefit end-product, wherein the end-product is at least partially based on the biomass availability, and wherein the end-product is at least partially based on a desired need; and producing the end-product from the biomass.

Figure 11:
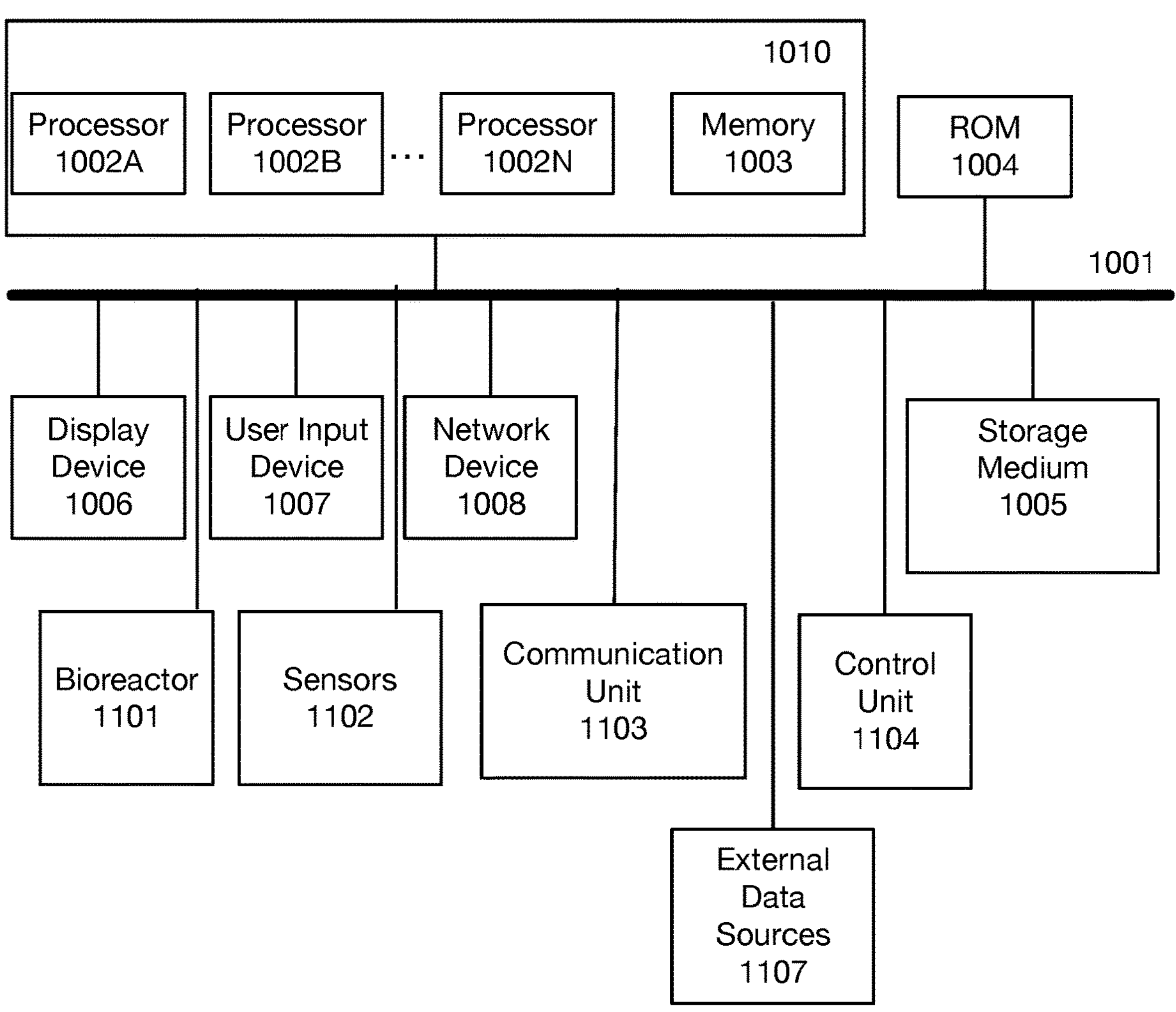
FIG. 11 is an exemplary system architecture that may be used in implementing the system and/or method.

FIG. 11 is an exemplary computer architecture diagram of one implementation of the system. In some implementations, the system is implemented in a plurality of devices in communication over a communication channel and/or network. In some implementations, the elements of the system are implemented in separate computing devices. In some implementations, two or more of the system elements are implemented in same devices. The system and portions of the system may be integrated into a computing device or system that can serve as or within the system.

The communication channel 1001 interfaces with the processors 1002A-1202N, the memory (e.g., a random access memory (RAM)) 1003, a read only memory (ROM) 1004, a processor-readable storage medium 1005, a display device 1006, a user input device 1007, and a network device 1008. As shown, the computer infrastructure may be used in one or more bioreactors 1101, sensors 1102, communication unit 1103, a control unit 1104, external data sources 1105, and/or other suitable computing devices.

The processors 1002A-1002N may take many forms, such CPUs (Central Processing Units), GPUs (Graphical Processing Units), microprocessors, ML/DL (Machine Learning/Deep Learning) processing units such as a Tensor Processing Unit, FPGA (Field Programmable Gate Arrays, custom processors, and/or any suitable type of processor.

The processors 1002A-1002N and the main memory 1003 (or some sub-combination) can form a processing unit 1010. In some embodiments, the processing unit includes one or more processors communicatively coupled to one or more of a RAM, ROM, and machine-readable storage medium; the one or more processors of the processing unit receive instructions stored by the one or more of a RAM, ROM, and machine-readable storage medium via a bus; and the one or more processors execute the received instructions. In some embodiments, the processing unit is an ASIC (Application-Specific Integrated Circuit). In some embodiments, the processing unit is a SoC (System-on-Chip). In some embodiments, the processing unit includes one or more of the elements of the system.

A network device 1008 may provide one or more wired or wireless interfaces for exchanging data and commands between the system and/or other devices, such as devices of external systems. Such wired and wireless interfaces include, for example, a universal serial bus (USB) interface, Bluetooth interface, Wi-Fi interface, Ethernet interface, near field communication (NFC) interface, satellite interface, cellular network interface, Global Positioning System (GPS), and the like.

Computer and/or Machine-readable executable instructions comprising of configuration for software programs (such as an operating system, application programs, and device drivers) can be stored in the memory 1003 from the processor-readable storage medium 1005, the ROM 1004 or any other data storage system.

When executed by one or more computer processors, the respective machine-executable instructions may be accessed by at least one of processors 1002A-1002N (of a processing unit 1010) via the communication channel 1001, and then executed by at least one of processors 1002A-1002N. Data, databases, data records or other stored forms data created or used by the software programs can also be stored in the memory 1003, and such data is accessed by at least one of processors 1002A-1002N during execution of the machine-executable instructions of the software programs.

The processor-readable storage medium 1005 is one of (or a combination of two or more of) a hard drive, a flash drive, a DVD, a CD, an optical disk, a floppy disk, a flash storage, a solid state drive, a ROM, an EEPROM, an electronic circuit, a semiconductor memory device, and the like. The processor-readable storage medium 1005 may additionally be remotely hosted and accessed over the communication channel 1001 or any suitable network. The processor-readable storage medium 1005 can include an operating system, software programs, device drivers, and/or other suitable sub-systems or software.

As used herein, first, second, third, etc. are used to characterize and distinguish various elements, components, regions, layers and/or sections. These elements, components, regions, layers and/or sections should not be limited by these terms. Use of numerical terms may be used to distinguish one element, component, region, layer and/or section from another element, component, region, layer and/or section. Use of such numerical terms does not imply a sequence or order unless clearly indicated by the context. Such numerical references may be used interchangeable without departing from the teaching of the embodiments and variations herein.

As a person skilled in the art will recognize from the previous detailed description and from the figures and claims, modifications and changes can be made to the embodiments of the invention without departing from the scope of this invention as defined in the following claims.

We claim:

1. A method for a reactor-based biomass processing comprising:

over a network of bioreactors, for each bioreactor, detecting a biomass input, comprising:

detecting the biomass type, detecting the biomass quality, comprising detecting the biomass composition including the biomass moisture content, and detecting the biomass quantity;

determining an optimized end-product, wherein the end-product is at least partially based on: a selected production target, the biomass input, and on local conditions at the location of each bioreactor; and producing the end-product, comprising:

monitoring reaction conditions, configuring a reactor of the network of bioreactors for the output production, based at least partially on biomass input, wherein configuring the reactor includes adjusting an oxygen flow rate into the reactor, and implementing a biomass decomposition;

wherein the method is implemented over the network of bioreactors such that determining the optimized end-product for each bioreactor is dependent on the network of bioreactors as a whole, and each bioreactor is individually configured to produce an end-product based on the network-wide determination.

2. The method of claim 1, wherein the biomass input comprises multiple biomasses.

3. The method of claim 1, wherein the optimized end-product comprises multiple end-products.

4. The method of claim 3, wherein the multiple end-products comprise heat energy and activated carbon.

5. The method of claim 1, wherein determining an optimized end-product is dependent on the entire network, and wherein the biomass input and the local conditions at the location of each bioreactor are unique to each reactor, and wherein the network of bioreactors comprises at least a first subset of bioreactors and a second subset of bioreactors, each subset configured to produce an end-product different from another subset.

6. The method of claim 5, wherein the method may be implemented remotely.

7. The method of claim 1, wherein the implementing the biomass decomposition comprises converting the biomass at least partially into heat energy.

8. The method of claim 7, wherein the heat energy production is coupled to a second reaction, thereby converting a compound into the optimized end-product by using the heat energy.

9. The method of claim 7, wherein the implementing the biomass decomposition comprises converting the biomass at least partially into activated carbon.

10. The method of claim 9, wherein the biomass input comprises agricultural residue.

11. The method of claim 10, wherein the agricultural residue comprises coconut residue.

12. The method of claim 1, wherein the optimized end-product comprises a fertilizer, and wherein determining the optimized end-product fertilizer is at least partially based on: the biomass input, current soil conditions, and a selected farm crop to grow.

13. The method of claim 12, wherein the biomass input comprises rice residue.

14. The method of claim 13, wherein the detecting the biomass input is an iterated process over multiple applications of the method, such that details regarding the biomass input improve over iterations.

* * * * *